United States Patent [19]

Bindra

[11] 4,213,907
[45] Jul. 22, 1980

[54] PROSTAGLANDIN INTERMEDIATES

[75] Inventor: Jasjit S. Bindra, Groton, Conn.

[73] Assignee: Pfizer Inc., New York, N.Y.

[21] Appl. No.: 661,270

[22] Filed: Feb. 25, 1976

[51] Int. Cl.² ............................................. C07D 307/77
[52] U.S. Cl. ...................... 260/343.3 P; 260/343.3 R; 542/426
[58] Field of Search ...................... 260/343.3, 343.3 P

[56] References Cited

FOREIGN PATENT DOCUMENTS 50-18459  2/1975  Japan .
50-18460  2/1975  Japan .

Primary Examiner—Natalie Trousof
Assistant Examiner—Jane T. Fan
Attorney, Agent, or Firm—Connolly and Hutz

[57] ABSTRACT

Certain novel 2-[1-hydroxycyclopent-2-yl]acetic acid γ-lactone derivatives are useful as intermediates for the synthesis of naturally-occurring prostaglandins and their analogues.

2 Claims, No Drawings

PROSTAGLANDIN INTERMEDIATES

BACKGROUND OF THE INVENTION

This invention relates to certain new chemical compounds. More particularly, it relates to certain derivatives of 2-[1-hydroxycyclopent-2-yl]-acetic acid γ-lactone, which are useful as intermediates for the synthesis of naturally-occurring prostaglandins and certain analogues thereof.

The naturally-occurring prostaglandins are derivatives of the C-20 fatty acid 7-[2β-octylcyclopent-1α-yl]heptanoic acid, which is also known as prostanoic acid and is depicted as follows:

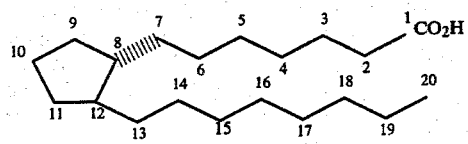

The naturally-occurring prostaglandins cause a wide variety of medicinally useful biological and pharmacological responses, both in vitro and in vivo, with the particular effect being determined by the precise chemical structure of the individual compound. Chemical modification of several of the naturally-occurring compounds has led to many additional derivatives (analogues), also having useful pharmacological properties. (See further: Bergstrom et al., *Pharmacological Reviews*, 20, 1 (1968) and Caton, *Progress in Medicinal Chemistry*, Butterworths Publications Ltd., London, 1971, Volume 8, page 317).

The so-called naturally-occurring prostaglandins have been isolated from a variety of mammalian sources. However, more recently, they have become available, together with a variety of analogues thereof, by total chemical synthesis from simple, readily-available, organic precursors. Although several basic synthetic routes to prostaglandin type compounds have been disclosed in the prior art, a series of publications by Corey et al. report one particular scheme which utilizes as intermediates certain bicyclic aldehydes of the formula:

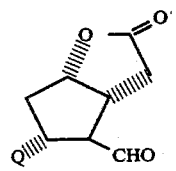

and the enantiomers thereof, wherein Q is hydrogen or a protected hydroxy group (e.g. tetrahydropyran-2-yloxy or dimethyl-t-butylsilyloxy). In one variation of the Corey et al. synthetic scheme, the said aldehyde of Formula I is condensed with a phosphonate ylid, to give a compound of the formula:

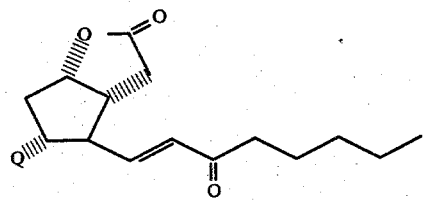

wherein Q is as previously defined, thereby introducing the eight carbon atoms required in the C-12 side chain of the natural prostaglandins. See, for example, Corey et al., *Journal of the American Chemical Society*, 91, 5675 (1969); ibid, 92, 397 (1970); ibid, 93, 1490 (1971); ibid, 93, 1491 (1971); *Journal of Organic Chemistry*, 37, 3043 (1972); and ibid, 39, 256 (1974). The present invention provides, as intermediates both for naturally-occurring prostaglandins and their analogues, bicyclic aldehydes of the formula:

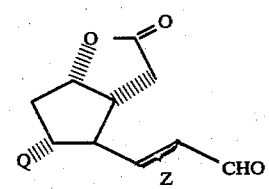

and the enantiomers thereof, wherein Z represents a single bond or a trans double bond, and Q is hydrogen or a protected hydroxy group, such as tetrahydropyran-2-yloxy or dimethyl-t-butylsilyloxy.

Unexamined Japanese patent applications Nos. 50-18,459 and 50-18,460, published Feb. 26, 1975, disclose the preparation of compounds of the formula IV, wherein R is a protecting group easily removable under acidic conditions (e.g. tetrahydropyran-2-yl), and also the subsequent reaction of the said compounds of formula IV with alkyl Grignard reagents. However, that embodiment of the present invention which involves the preparation of the compound of formula IV, wherein R is tetrahydropyran-2-yloxy and its reaction with n-pentyl magnesium bromide, had been completed in this country prior to Feb. 26, 1975.

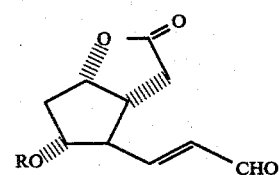

SUMMARY OF THE INVENTION

It is an object of this invention to provide chemical compounds of the formula

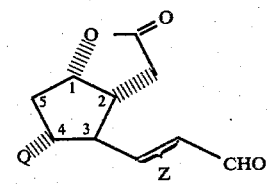

and the enantiomers thereof, wherein Z represents a single bond or a trans double bond, and Q is hydrogen or a protected hydroxy group, wherein the protecting group is removable under mildly acidic conditions, said compounds of formula III being useful as intermediates in the synthesis of naturally-occurring prostaglandins and certain analogues thereof. However, the preferred compounds of the invention are those compounds having the absolute stereochemistry (absolute configuration) shown in formula III. The preferred protected hydroxy groups are tetrahydropyran-2-yloxy and dimethyl-t-butylsilyloxy.

DETAILED DESCRIPTION OF THE INVENTION

The compounds of this invention are the compounds of formula III and, as will be appreciated by one skilled in the art, the compounds of formula III possess several centers of asymmetry (asymmetrically-substituted carbon atoms). Throughout this specification, broken line attachments of a substituent to the cyclopentane ring of a compound of formula III, and all other cyclopentane derivatives, is intended to indicate that the substituent is below the plane of the cyclopentane ring. Such attachment is also referred to as the alpha configuration (α-configuration). Conversely, solid line attachment of a substituent to the cyclopentane ring of the cyclopentane compounds in this specification is intended to indicate attachment of that substituent above the plane of the 5-membered ring. This latter attachment is also called the beta configuration (β-configuration). As written above, therefore, a compound of formula III represents a single isomer, and it represents a single isomer having absolute configurations (absolute stereochemistries) at positions 1, 2, 3 and 4, respectively, corresponding to those at positions 9, 8, 12 and 11, respectively, of the naturally-occurring prostaglandins of the F group (e.g. PGF$_{1\alpha}$, PGF$_{2\alpha}$ and PGF$_{3\alpha}$) obtained from mammalian tissues. Cyclopentane derivatives having absolute configurations at positions 1, 2, 3 and 4 corresponding to those found in naturally-occurring prostaglandins are referred to as compounds of natural configuration. Compounds which have absolute configurations at positions 1, 2, 3 and 4, each of which is the reverse of that found in the naturally-occurring prostaglandins, are referred to as compounds of enantiomeric configuration. The natural compounds are, of course, related to the enantiomeric compounds as object and mirror image.

In one method according to the invention, the compounds of the formula III, wherein Z represents a trans double bond, are prepared by reaction of the appropriate compound of formula I with (formylmethylene)-dimethylphenylphosphorane (V) viz:

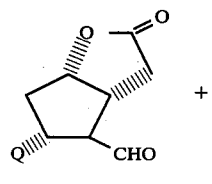

I

+

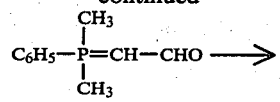

V

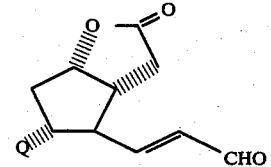

The reaction is usually carried out by contacting the aldehyde of formula I with about two molar equivalents of the (formylmethylene)dimethylphenyl-phosphorane, in a reaction-inert organic solvent, at a temperature in the range from about −20° C. to about 80° C., until reaction is substantially complete. An appropriate reaction-inert solvent is one which will substantially dissolve at least one of the starting materials, and which does not adversely affect either the starting materials or the product. Typical solvents which are used are aromatic hydrocarbons, such as benzene and toluene, and chlorinated hydrocarbons, such as methylene chloride and chloroform. At about −20° C. the reaction commonly takes several days (e.g. about 3 days) to reach completion; at about 80° C. the reaction is usually complete within a few hours (e.g. about 2 hours). The product is readily isolable by standard procedures, for example by evaporation of the solvent in vacuo. It can be used further in the crude state, or if desired it can be purified using well-known techniques such as recrystallization and/or chromatography. Column chromatography using silica gel as the absorbent is a particularly convenient and effective method of product purification.

In one method according to the invention, the compounds of formula III, wherein Z is a single bond, are prepared by hydrogenation of the corresponding compound of the formula III, wherein Z represents trans double bond, viz:

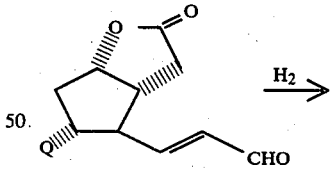

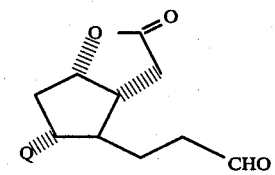

The reaction is a conventional hydrogenation reaction, and it is usually carried out by stirring or shaking a solution of the compound of the formula III, wherein Z represents a trans double bond, under an atmosphere of hydrogen, or hydrogen mixed with an inert diluent such as nitrogen or argon, in the presence of a catalytic amount of an appropriate metal catalyst. Typical metal catalysts which can be used are rhodium, palladium and platinum, with the preferred agent being palladium.

Convenient solvents are lower alkanols such as methanol and ethanol, ethers such as diethyl ether and tetrahydrofuran and low molecular weight esters such as ethyl acetate and butyl acetate. The hydrogenation is usually conducted at or about atmospheric pressure, and at or about 25° C. The palladium catalyst is conveniently used in the form of a 10% suspension on carbon and is usually present in an amount from about 10 to about 50 mole-percent based on the compound of formula III. Under these conditions, reaction times of a few hours (e.g. about 3 hours) are usually required. The hydrogenated product can be recovered simply by removing the catalyst by filtration and then removing the solvent by evaporation in vacuo. The product thus obtained can be used directly, or it can be purified by such well-known techniques as recrystallization and/or chromatography.

As will be appreciated by one with skill in the art, conversion of compound of the formula I into a compound of the formula III by reaction with the phosphonium ylid V, does not affect any of the asymmetric centers in the molecule. Similarly, hydrogenation of a compound of the formula III, wherein Z represents a trans double bond, to give a compound of the formula III, wherein Z is a single bond, does not affect any of the asymmetric centers in the molecule. Accordingly, when it is desired to prepare a compound of formula III it is necessary to use a starting material having the natural configuration. In like manner, an enantiomer of a compound of the formula III is prepared from a starting material of enantiomeric configuration.

In the compounds of this invention, the group Q can be hydrogen or a protected hydroxy group. When Q is a protected hydroxy group, the protecting group is an acid-labile protecting group of which the tetrahydropyran-2-yl and the dimethyl-t-butylsilyl groups are especially useful.

The starting materials for the preparation of the compounds of the formula III, wherein Z represents a trans double bond, are either known compounds, which are prepared by the published procedures, or they are analogues of known compounds, which are prepared by simple modifications of published procedures. Thus, the compound of the formula I, wherein Q is tetrahydropyran-2-yloxy is prepared according to the Scheme A.

SCHEME A

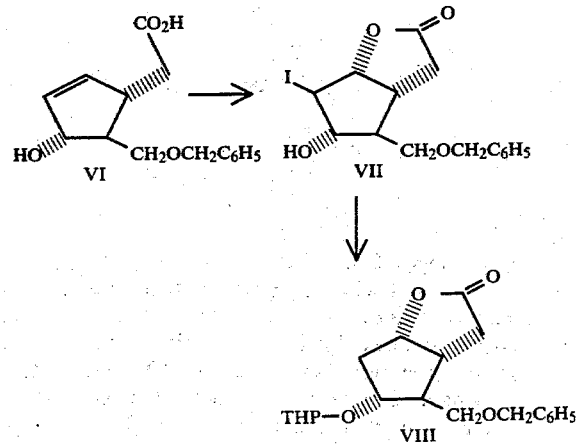

-continued
SCHEME A

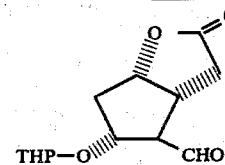

wherein THP represents the tetrahydropyran-2-yl group. In Scheme A, the carboxylic acid VI is iodolactonized as described by Corey et al. (Journal of the American Chemical Society, 93, 1491 [1971]), and then the iodolactone VII is converted into its tetrahydropyran-2-yl ether by reaction with dihydropyran and a catalytic amount of 4-toluenesulfonic acid. The tetrahydropyranylated derivative of VII is then de-iodinated using tributyltin hydride, in a manner analogous to that described by Corey et al. for de-iodination of the corresponding racemic compound with a methoxymethyl group at the 3-position and an acetoxy group at the 4-position (Journal of the American Chemical Society, 91 5675 [1969]). Conversion of the lactone VIII into the compound of formula I, wherein Q is tetrahydropyran-2-yloxy, is carried out by hydrogenolytic removal of the benzyl group, followed by oxidation, as described by Corey et al. (Journal of the American Chemical Society, 93, 1490 [1971]).

The compound of formula I, wherein Q is dimethyl-t-butylsilyloxy, is prepared in exactly the same manner as the compound of formula I, wherein Q is tetrahydropyran-2-yloxy, except that the intermediate of formula VII is reacted with dimethyl-t-butylsilyl chloride, rather than dihydropyran, before being de-iodinated, debenzylated and oxidized. See further: Corey et al., Journal of the American Chemical Society, 94, 6190 (1972).

The enantiomers of the compounds of the formula I, wherein Q is tetrahydropyran-2-yloxy and dimethyl-t-butylsilyloxy, are prepared in a manner analogous to the method just described for the compounds of natural configuration, except that the enantiomer of the carboxylic acid VI is used as the starting material. Preparation of the enantiomer of the compound of the formula VI is described by Corey et al., Journal of Organic Chemistry, 37, 3043 (1972).

The compound of formula I, wherein Q is hydrogen, is prepared from either the iodolactone VII or from the unsaturated lactone IX, using the methods described by Corey et al. (Journal of Organic Chemistry, 39, 256 [1974]). The enantiomer of the compound of the formula I, wherein Q is hydrogen, is prepared in a manner analogous to those used for the compound of natural configuration, except that the enantiomeric compound of formula VII or IX is used as starting material.

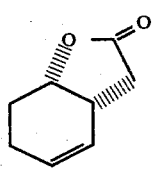 (IX)

(Formylmethylene)dimethylphenylphosphorane is prepared by: (1) alkylation of dimethylphenylphosphine with methyl bromide; (2) treatment of the trimethylphenylphosphonium bromide thus formed with one equivalent of butyllithium; (3) formylation of the methylenedimethylphenylphosphorane thus formed with ethyl formate; and (4) treatment of the (formylmethyl)-dimethylphenylphosphonium salt thus formed with sodium hydroxide.

As indicated hereinbefore, the compounds of formula III are useful as intermediates for the synthesis of medicinally-useful naturally-occurring prostaglandins or certain medicinally-useful analogues thereof.

Thus, the compounds of formula III, wherein Z represents a trans double bond and Q is tetrahydropyran-2-yloxy or dimethyl-t-butylsilyloxy can be converted into prostaglandins PGE$_2$ and PGF$_{2\alpha}$ by the method schown in Scheme B.

configuration (i.e. the hydroxy group is in the α-configuration by prostaglandin stereochemical notation), is then bis-tetrahydropyranylated to give XIII. Finally, XIII can be converted into prostaglandins PGF$_{2\alpha}$ and PGE$_2$ by the method of Corey et al., Journal of the American Chemical Society, 92, 397 (1970). Prostaglandins PGE$_2$ and PGF$_{2\alpha}$ are useful abortifacient agents.

The compounds of formula III, wherein Z represents a single bond and Q is tetrahydropyranyloxy or dimethyl-t-butylsilyloxy are converted into 13,14-dihydro-16-phenyl-ω-tetranorprostaglandin PGE$_2$ (XVII), by the method shown in Scheme C.

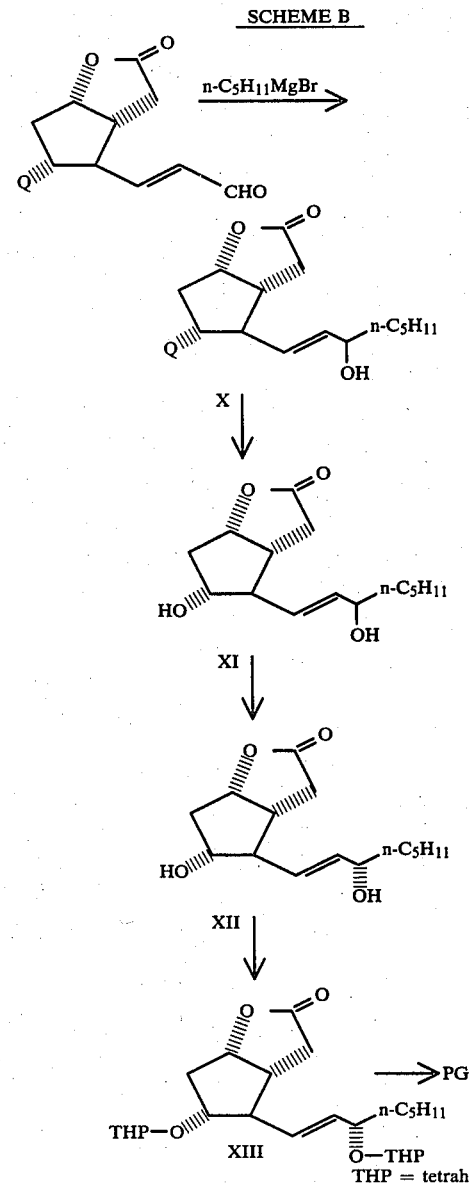

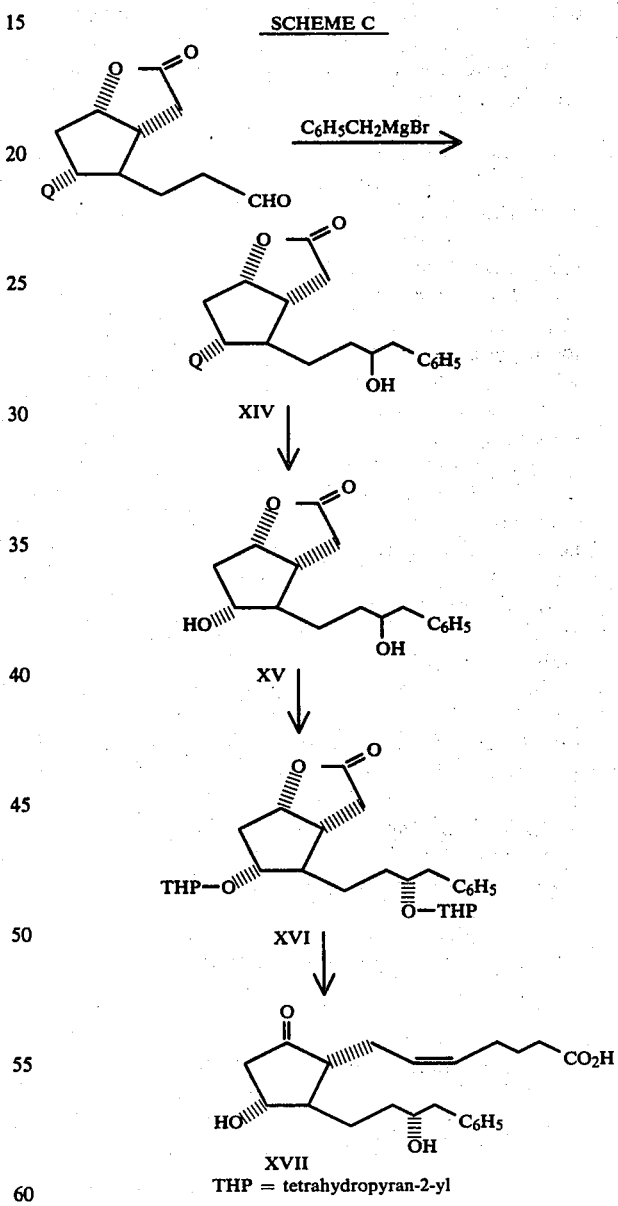

THP = tetrahydropyran-2-yl

According to Scheme B, the said compound of formula III is reacted with n-pentyl magnesium bromide to give the compound X, as a mixture of epimers at the 3-position of the 3-hydroxyoct-1-enyl side-chain. The protecting group is then removed from the group Q, to give XI, which is separated into its individual epimers by chromatography. The more polar epimer XII, which has the asymmetric center in the C-3 side chain in the S According to Scheme C, the said compound of formula III is reacted with benzyl magnesium bromide to give compound XIV, as a mixture of epimers in the 3-hydroxy-4-phenylbutyl side-chain. The protecting group is removed from Q, to give XV, and the epimers are separated by chromatography. The more polar epimer is converted into its bis-tetrahydropyranyl ether derivative XVI, which is converted into 13,14-dihydro-16-phenyl-ω-tetranorprostaglandin PGE₂ (XVII), by the method described in Belgian patent No. 802,231. 13,14-Dihydro-16-phenyl-ω-tetranorprostaglandin PGE₂ is useful for lowering blood pressure in mammals, as taught in the said Belgian patent.No. 802,231.

The compounds of formula III, wherein Q is hydrogen, are useful as intermediates for the preparation of 13,14-dihydro-16-phenyl-11-deoxy-ω-tetranorprostagladin PGE₂ (XX), by the method shown in Scheme D.

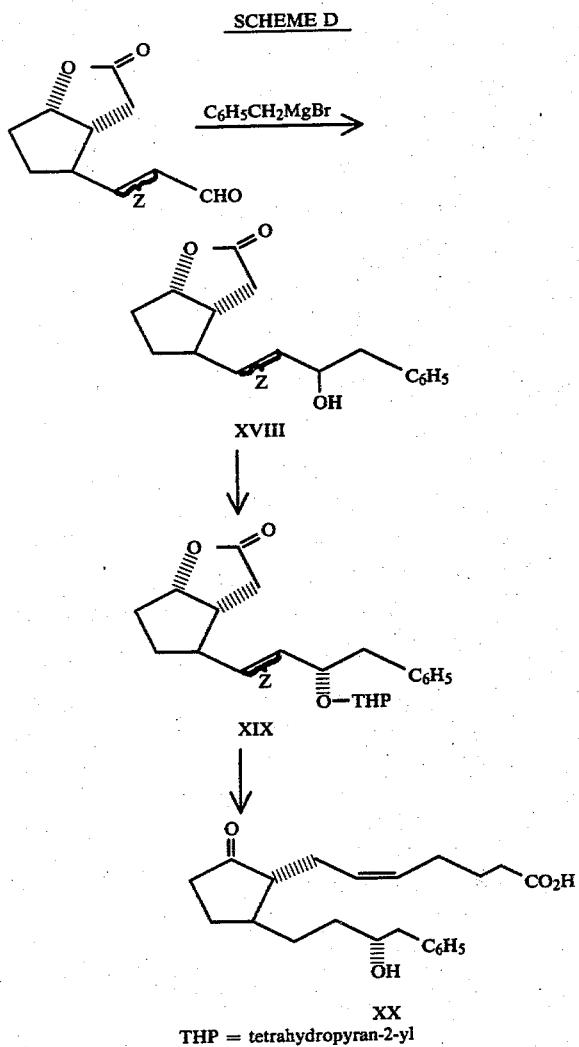

SCHEME D

THP = tetrahydropyran-2-yl

According to Scheme D, the compound of the formula III, wherein Q is hydrogen, is reacted with benzyl magnesium bromide to give compound XVIII, as a mixture of epimers in the 3-hydroxy-4-phenylbut-1-enyl or 3-hydroxy-4-phenylbutyl side-chain. The mixture of epimers is separated, and the less-polar epimer is converted into its tetrahydropyranyl ether, in each case. This produces 2-[1α-hydroxy-3β-(3-[tetrahydropyran-2-yloxy]-4-phenylbut-1-enyl)cyclopent-2α-yl]acetic acid γ-lactone (XIX, Z represents a trans double bond), and 2-[1α-hydroxy-3β-(3-[tetrahydropyran-2-yloxy]-4-phenylbutyl)cyclopent-2α-yl]acetic acid γ-lactone (XIX, Z represents a single bond). The compounds XIX, wherein Z represents a trans double bond or a single bond, can each be converted into 13,14-dihydro-16-phenyl-11-deoxy-ω-tetranorprostaglandin PGE₂ (XX) by methods taught in United States patent application No. 531,676. For conversion of XIX into XX in the case wherein Z represents a single bond, the conversion is carried out in a manner analogous to that used for conversion of XIII to PGE₂. For conversion of XIX into XX in the case wherein Z represents a trans double bond, the said trans double bond is first hydrogenated to give the compounds of formula XIX, wherein Z represents a single bond; the method used for conversion of XIII into PGE₂ can then be used to complete the conversion into XX. Compound XX is useful for lowering blood pressure in hypertensive mammals. For the treatment of hypertension, compound XX is administered by intravenous injection at doses of about 0.5 to 10 mcg./kg., or preferably in the form of capsules or tablets at doses of 0.005 to 0.5 mg./kg./day.

The following examples are given solely for the purpose of further illustration.

EXAMPLE I

2-[4α-(Tetrahydropyran-2-yloxy)-1α-hydroxy-3β-(3-oxo-transprop-1-enyl)cyclopent-2α-yl]acetic Acid, γ-Lactone A mixture of 1.01 g. (4 mmol) 2-[4α-(tetrahydropyran-2-yloxy)-1α-hydroxy-3β-formylcyclopent-2α-yl]acetic acid γ-lactone (natural configuration) and 2.3 g. of (formylmethylene)dimethylphenylphosphorane in 30 ml. of benzene was heated under reflux for 0.5 hr., and then an additional 1.5 g. of ylid in 10 ml. of benzene was added. Refluxing was continued for 1.0 hr., and then the solvent was removed by evaporation in vacuo. The residue was purified by column chromatography on silica gel, using methylene chloride-methanol (95:5) as eluent. Evaporation of the appropriate fractions gave the product as a pale yellow oil, $R_f$ 0.70 (9:1 $CH_2Cl_2:CH_3OH$). IR: 1775 cm⁻¹ (lactone carbonyl) and 1690 cm⁻¹ (aldehyde carbonyl). NMR: 6.05 δ (1H, C$\underline{H}$-CHO, double doublet, J=7 and J=16 Hz) and 9.4 δ (1H, C$\underline{H}$O, doublet, J=7 Hz).

The above product has absolute configurations at positions 1, 2, 3 and 4 corresponding to the absolute configurations at 9, 8, 12 and 11, respectively, of the natural prostaglandins. The enantiomer of the title product is prepared using the above procedure, but employing 2-[4β-(tetrahydropyran-2-yloxy)-1β-hydroxy-3α-formylcyclopent-2β-yl]acetic acid γ-lactone and (formylmethylene)dimethylphenylphosphorane as starting materials.

EXAMPLE II

2-[4α-(Dimethyl-t-butylsilyloxy)-1α-hydroxy-3β-(3-oxo-trans-prop-1-enyl)cyclopent-2α-yl]acetic Acid γ-Lactone 2-[4α-(Dimethyl-t-butylsilyloxy)-1α-hydroxy-3β-(3-oxo-trans-prop-1-enyl)cyclopent-2α-yl]acetic acid γ-lactone is prepared by reaction of 2-[4α-(dimethyl-t-butylsilyloxy)-1α-hydroxy-3β-formylcyclopent-2α-yl]acetic acid γ-lactone with (formylmethylene)dimethylphenylphosphorane, using the procedure of Example I.

EXAMPLE III

2-[4β-(Dimethyl-t-butylsilyloxy)-1β-hydroxy-3α-(3-oxo-trans-prop-1-enyl)cyclopent-2β-yl]acetic Acid γ-Lactone The title product is prepared by reaction of 2-[4β-(dimethyl-t-butylsilyloxy)-1β-hydroxy-3α-formylcyclopent-2β-yl]acetic acid γ-lactone with (formylmethylene)dimethylphenylphosphorane, according to the procedure of Example I.

EXAMPLE IV

2-[1α-Hydroxy-3β-(3-oxo-trans-prop-1-enyl)cyclopent-2α-yl]acetic Acid γ-Lactone

To a solution of 1.08 g. (6 mmol) of (formylmethylene)dimethylphenylphosphorane, in 15 ml. of methylene chloride, cooled to $-5°$ C., was added dropwise a solution of 462 mg. (3 mmol) of 2-[1α-hydroxy-3β-formylcyclopent-2α-yl]acetic acid γ-lactone in 10 ml. of methylene chloride. The reaction mixture was stored at $-20°$ C. for 72 hr., and then it was warmed to 25° C. and diluted with further methylene chloride. The resulting solution was washed with water, dried using anhydrous sodium sulfate, and then evaporated in vacuo. The residue was purified by chromatography on silica gel using cyclohexane:isopropanol as eluent. This afforded 207 mg. of the title compound as a crystalline solid. After recrystallization from ether it had m.p. 52°–54° C.

EXAMPLE V

2-[1β-Hydroxy-3α-(3-oxo-trans-prop-1-enyl)cyclopent-2β-yl]acetic acid γ-Lactone

The title compound is prepared by reaction of 2-[1β-hydroxy-3α-formylcyclopent-2β-yl]acetic acid γ-lactone with (formylmethylene)dimethylphenylphosphorane, according to the procedure of Example IV.

EXAMPLE VI

2-[4α-(Tetrahydropyran-2-yloxy)-1α-hydroxy-3β-(3-oxopropyl)cyclopent-2α-yl]acetic Acid γ-Lactone A mixture of 1.1 g. (3.5 mmol) of 2-[4α-(tetrahydropyran-2-yloxy)-1α-hydroxy-3β-(3-oxo-trans-prop-1-enyl)cyclopent-2α-yl]acetic acid γ-lactone, 100 mg. of 10% palladium-on-carbon and 30 ml. of ethanol was stirred under an atmosphere of hydrogen, at atmospheric pressure, for 3 hr. The filtered reaction mixture was evaporated in vacuo to give the crude product as an oil. The crude product was purified by chromatography on 30 g. of silica gel, using ether as the eluent. This afforded 800 mg. of pure title product. NMR: 9,30 δ (1H, singlet); IR 1775 and 1740 cm$^{-1}$.

EXAMPLE VII

2-[4β-(Tetrahydropyran-2-yloxy)-1B-hydroxy-3α-(3-oxopropyl)cyclopent-2β-yl]acetic Acid γ-Lactone 2-[4β-(Tetrahydropyran-2-yloxy)-1β-hydroxy-3α-(3-oxopropyl)cyclopent-2β-yl]acetic acid γ-lactone is prepared by hydrogenation of 2-[4β-tetrahydropyran-2-yloxy)-1β-hydroxy-3α-(3-oxo-trans-prop-1-enyl)cyclopent-2β-yl]acetic acid γ-lactone, using the procedure of Example VI.

EXAMPLE VIII

2[4α-(Dimethyl-t-butylsilyloxy)-1α-hydroxy-3β-(3-oxopropyl)cyclopent-2α-yl]acetic Acid γ-Lactone 2-[4α-(Dimethyl-t-butylsilyloxy)-1α-hydroxy-3β-(3-oxopropyl)cyclopent-2α-yl]acetic acid γ-lactone is prepared by hydrogenation of 2-[4α-(dimethyl-t-butylsilyloxy)-1α-hydroxy-3β-(3-oxo-trans-prop-1-enyl)cyclopent-2α-yl]acetic acid γ-lactone, using the method of Example VI.

EXAMPLE IX

2-[4β-(Dimethyl-t-butylsilyloxy)-1β-hydroxy-3α-(3-oxopropyl)cyclopent-2β-yl]acetic Acid γ-Lactone The title compound is prepared by hydrogenation of 2-[4β-(dimethyl-t-butylsilyloxy)-1β-hydroxy-3α-(3-oxoprop-1-enyl)cyclopent-2β-yl]acetic acid γ-lactone, according to the procedure of Example VI.

EXAMPLE X

2-[1α-Hydroxy-3β-(3-oxopropyl)cyclopent-2α-yl]acetic Acid γ-Lactone

2-[1α-Hydroxy-3β-(3-oxopropyl)cyclopent-2α-yl]acetic acid γ-lactone is prepared by hydrogenation of 2-[1α-hydroxy-3β-(3-oxo-trans-prop-1-enyl)cyclopent-2α-yl]acetic acid γ-lactone, by using the procedure of Example VI.

EXAMPLE XI

2-[1β-Hydroxy-3α-(3-oxopropyl)cyclopent-2β-yl]acetic Acid γ-Lactone

The title compound is prepared by hydrogenation of 2-[1β-hydroxy-3α-(3-oxo-trans-prop-1-enyl)cyclopent-2β-yl]acetic acid γ-lactone, using the procedure of Example VI.

EXAMPLE XII

2-[4α-(Tetrahydropyran-2-yloxy)-1α-hydroxy-3β-(3-hydroxy-trans-oct-1-enyl)cyclopent-2α-yl]acetic Acid γ-Lactone To a solution of 0.76 g. (2.7 mmol) of 2-[4α-(tetrahydropyran-2-yloxy)-1α-hydroxy-3β-(3-oxo-trans-prop-1-enyl)cyclopent-2α-yl]acetic acid, γ-lactone in 20 ml. of dry tetrahydrofuran, under nitrogen, was added dropwise 0.82 ml. of a 3 M solution of n-pentyl magnesium bromide in ether. After five minutes, the reaction was quenched by the addition of saturated aqueous ammonium chloride followed by methylene chloride (50 ml.), washing with brine (10 ml.), dried with sodium sulfate and concentrated to an oil. This afforded the title compound as a mixture of epimers at the newly introduced asymmetric center in the C-3 side chain.

EXAMPLE XIII

2-[1α,4α-Dihydroxy-3β-(3-hydroxy-trans-oct-1-enyl)-cyclopent-2α-yl]acetic Acid γ-Lactone A solution of 500 mg. of 2-[4α-(tetrahydropyran-2-yloxy)-1α-hydroxy-3β-(3-hydroxy-trans-oct-1-enyl)cyclopent-2α-yl]acetic acid γ-lactone (the product of Example XII) is dissolved in 20 ml. of acetic acid-water-tetrahydrofuran (3:1:1), and the solution is maintained at 25° C. for 24 hours. The solvents are removed by evaporation in vacuo to give the title product as a mixture of epimers at the 3-position of the 3-hydroxyoct-1-enyl side chain. The mixture of epimers is separated by preparative thin-layer chromatography on silica gel, using ether as eluent.

The more polar epimer has the hydroxy group in the 3-hydroxyoct-1-enyl side chain in the α-configuration (prostaglandin stereochemical notation), and it can be converted into prostaglandins PGF$_{2α}$ and PGE$_2$ by the method of Corey et al., *Journal of the American Chemical Society*, 92, 397 (1970).

EXAMPLE XIV

2-[1α,4α-Dihydroxy-3β-(3-hydroxy-trans-oct-1-enyl)cyclopent-2α-yl]acetic Acid γ-Lactone 2-[4α-(Dimethyl-t-butylsilyloxy)-1α-hydroxy-3β-(3-oxo-trans-prop-1-enyl)cyclopent-2α-yl]acetic acid γ-lactone is reacted with n-pentyl magnesium bromide, according to the procedure of Example XII, and the product thus obtained is hydrolysed using acid-water-tetrahydrofuran, according to the procedure of Example XIII. The epimeric mixture obtained is separated by preparative thin-layer chromatography on silica gel, using ether as eluent. The more polar epimer is the title compound having the correct stereochemistry for conversion to PGF$_{2α}$ and PGE$_2$ by the method cited in Example XIII.

EXAMPLE XV

2-[1α,4α-Dihydroxy-3β-(3-hydroxy-4-phenylbutyl)cyclopent-2α-yl]acetic Acid γ-Lactone 2-[4α-(Tetrahydropyran-2-yloxy)-1α-hydroxy-3β-(3-oxypropyl)cyclopent-2α-yl]acetic acid γ-lactone is reacted with benzyl magnesium bromide, according to the procedure of Example XII, and the product thus obtained is hydrolysed using acetic acid-water-tetrahydrofuran, according to the procedure of Example XIII. This affords 2-[1α,4α-dihydroxy-3β-(3-hydroxy-4-phenylbutyl)cyclopent-2α-yl]acetic acid γ-lactone as a mixture of epimers at the 3-position of the 3-hydroxy-4-phenylbutyl side-chain. The epimers are separated by thin-layer chromatrography using silica gel as absorbent.

In like manner, reaction of 2-[4α-(dimethyl-t-butylsilyloxy)-1α-hydroxy-3β-(3-oxopropyl)cyclopent-2α-yl]acetic acid γ-lactone is reacted with benzyl magnesium bromide, according to the procedure of Example VII, and the product thus obtained is hydrolysed using acetic acid-water-tetrahydrofuran, according to the procedure of Example XIII. This also affords 2-[1α,4α-dihydroxy-3β-(3-hydroxy-4-phenylbutyl)cyclopent-2α-yl]acetic acid γ-lactone as a mixture of epimers at the 3-position of the 3-hydroxy-4-phenylbutyl side-chain.

EXAMPLE XVI

2-[1α,4α-Di(tetrahydropyran-2-yloxy)-3β-(3-hydroxy-4-phenylbutyl)cyclopent-2α-yl]acetic Acid γ-Lactone To a solution of 750 mg. of 2-[1α,4α-dihydroxy-3β-(3-hydroxy-4-phenylbutyl)cyclopent-2α-yl]acetic acid γ-lactone (the more polar epimer from Example XV) in 30 ml. of methylene chloride, at 0° C., is added 1.0 ml. of dihydropyran and 10 mg. of 4-toluenesulfonic acid. The solution is stored for 30 minutes as it is allowed to warm to 25° C. The solution is diluted with an equal volume of ether and then it is washed with sodium bicarbonate solution followed by water. The dried solution is evaporated in vacuo giving the title compound, which can be converted into 13,14-dihydro-16-phenyl-ω-tetranorprostaglandin PGE$_2$ by the method described in Belgian Pat. No. 802,231.

EXAMPLE XVII

2-[1α-Hydroxy-3β-(3-hydroxy-4-phenylbut-1-enyl)cyclopent-2α-yl]acetic Acid γ-Lactone Reaction of 2-[1α-hydroxy-3β-(3-oxo-trans-prop-1-enyl)cyclopent-2α-yl]acetic acid γ-lactone with benzyl magnesium bromide, using the procedure of Example XII, affords the title compound as a mixture of epimers at the 3-position of the 3-hydroxy-4-phenylbut-1-enyl side-chain. The epimers are separated by preparative thin-layer chromatography on silica gel, using ether as eluent.

EXAMPLE XVIII

2-[1α-Hydroxy-3β-(3-[tetrahydropyran-2-yloxy]-4-phenylbut-1-enyl)cyclopent-2α-yl]acetic Acid γ-Lactone 2-[1α-Hydroxy-3β-(3-hydroxy-4-phenylbut-1-enyl)-cyclopent-2α-yl]acetic acid γ-lactone (the less polar epimer from Example XVII) is tetrahydropyranylated using dihydropyran and a catalytic amount of 4-toluenesulfonic acid, according to the procedure of Example XVI. This affords the title product, which can be converted into 13,14-dihydro-16-phenyl-11-deoxy-ω-tetranorprostaglandin PGE$_2$, using the method disclosed in U.S. patent application Ser. No. 531,676.

EXAMPLE XIX

2-[1α-Hydroxy-3β-(3-hydroxy-4-phenylbutyl)cyclopent-2α-yl]acetic Acid γ-Lactone

Reaction of 2-[1α-hydroxy-3β-(3-oxopropyl)cyclopent-2α-yl]acetic acid γ-lactone with benzyl magnesium bromide, using the procedure of Example XII, affords the title compound as a mixture of epimers at the 3-position of the 3-hydroxy-4-phenylbutyl side-chain. The epimers are separated by preparative thin-layer chromatography on silica gel.

EXAMPLE XX

2-[1α-Hydroxy-3β-(3-[tetrahydropyran-2-yl]-4-phenylbutyl)cyclopent-2α-yl]acetic Acid γ-Lactone 2-[1α-Hydroxy-3β-(3-hydroxy-4-phenylbutyl)cyclopent-2α-yl]acetic acid γ-lactone (the less-polar epimer from Example XIX) is reacted with dihydropyran in methylene chloride, in the presence of a catalytic amount of 4-toluenesulfonic acid, using the procedure of Example XVI. This affords the title compound, which can be converted into 13,14-dihydro-16-phenyl-11-deoxy-ω-tetranorprostaglandin PGE$_2$ by the method described in U.S. patent application Ser. No. 531,676.

PREPARATION (Formylmethylene)dimethylphenylphosphorane

To a suspension of phenyltrimethylphosphonium bromide (5.8 g., 0.025 mole) (mp 257° C., prepared by reacting methyl bromide with phenyldimethylphosphine in toluene) in dry tetrahydrofuran (37 ml.) under nitrogen, at 0° C., was added n-butyl lithium (13.1 ml. of 1.9 M solution in hexane, 0.025 mole), dropwise, and the mixture was stirred for 20 minutes until homogeneous. A solution of ethyl formate (6 ml.) in tetrahydrofuran (12 ml.) was added in one portion, and the mixture was stirred for an additional 30 minutes. The mixture was poured into ice-cooled 1 N hydrochloric acid (62.5 ml.) and washed with cold ether (3×25 ml.) to remove unchanged reactants. The pH of the acidic layer was raised to 10 with cold 3 N sodium hydroxide, and the yield was extracted into methylene chloride. The methylene chloride solution was dried using sodium sulfate and then the solvent was removed by evaporation in vacuo, below 10° C. This afforded the title ylid as a yellow oil.

What is claimed is:

1. A compound of the formula

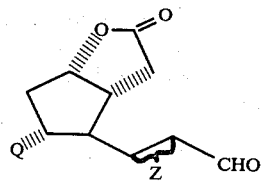

wherein Z is a trans double bond and Q is selected from the group consisting of tetrahydropyran-2-yloxy and dimethyl-t-butylsilyloxy.

2. The compound of claim 1 wherein Q is tetrahydropyran-2-yloxy.